United States Patent
Ponrathnam et al.

(10) Patent No.: US 9,505,700 B2
(45) Date of Patent: Nov. 29, 2016

(54) HIGH REFRACTIVE INDEX (METH) ACRYLATES

(71) Applicant: Council of Scientific & Industrial Research, New Delhi (IN)

(72) Inventors: Surendra Ponrathnam, Maharashtra (IN); Ravindra Vasant Ghorpade, Maharashtra (IN); Nayaku Nivrati Chavan, Maharashtra (IN); Rajan Chelanattukizhakkemadath, Maharashtra (IN); Sonali Madhavrao Bhosale, Maharashtra (IN); Sunil Sitaram Bhongale, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/409,812

(22) PCT Filed: Jun. 21, 2013

(86) PCT No.: PCT/IN2013/000387
§ 371 (c)(1),
(2) Date: Dec. 19, 2014

(87) PCT Pub. No.: WO2013/190575
PCT Pub. Date: Dec. 27, 2013

(65) Prior Publication Data
US 2015/0321991 A1    Nov. 12, 2015

(30) Foreign Application Priority Data
Jun. 21, 2012 (IN) .......................... 1915/DEL/2012

(51) Int. Cl.
*C07C 67/14* (2006.01)
*C07C 69/003* (2006.01)
(Continued)

(52) U.S. Cl.
CPC ............. *C07C 67/14* (2013.01); *C07C 69/003* (2013.01); *C07C 69/54* (2013.01); *C08F 120/68* (2013.01)

(58) Field of Classification Search
CPC ..... C07C 67/14; C07C 69/54; C07C 69/003; C08F 120/68
USPC ........................................................ 560/221
See application file for complete search history.

(56) References Cited

U.S. PATENT DOCUMENTS 6,359,170 B1 * 3/2002 Olson ................... C07C 69/653
                                                                        560/221
7,271,283 B2 * 9/2007 Chisholm ............. C07C 323/12
                                                                        560/121

(Continued)

FOREIGN PATENT DOCUMENTS

| EP | 0519410 | 12/1992 |
|---|---|---|
| WO | WO 99/07756 | * 2/1999 |
| WO | WO2010/074862 | 7/2010 |

OTHER PUBLICATIONS

National Center for Biotechnology Information. PubChem Substance Database; SID=125568822, https://pubchem.ncbi.nlm.nih.gov/substance/125568822, available online on Oct. 30, 2011 (accessed Mar. 9, 2016).*
PubChem CAS registry number search results, 1 pg, dated Mar. 9, 2016.*

(Continued)

*Primary Examiner* — Jafar Parsa
*Assistant Examiner* — Amy C Bonaparte
(74) *Attorney, Agent, or Firm* — McDonald Hopkins, LLC

(57) ABSTRACT

Novel aromatic hydrophobic (meth)acrylate monomers of Formula I having high refractive index (more than 1.55) are provided herein. The present invention further provides efficient and improved process for the preparation of aromatic hydrophobic monomers of Formula (I), wherein the high refractive index property can be advantageously used to make light weight optical materials with high transparency.

Formula (I)

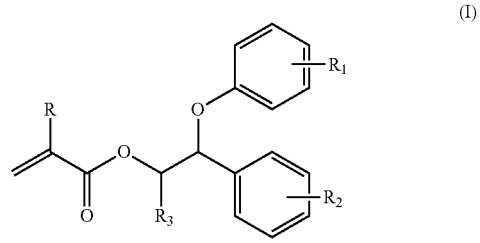

13 Claims, 8 Drawing Sheets

(51) Int. Cl.
*C08F 120/68* (2006.01)
*C07C 69/54* (2006.01)

(56) References Cited

U.S. PATENT DOCUMENTS

| | | | |
|---|---|---|---|
| 7,714,090 B2* | 5/2010 | Iwamoto | C07C 67/08 526/259 |
| 8,742,159 B2* | 6/2014 | Hoshino | C07C 69/92 526/247 |
| 2008/0021129 A1 | 1/2008 | Cordova et al. | |
| 2008/0139769 A1 | 6/2008 | Iwamoto et al. | |
| 2012/0053313 A1 | 3/2012 | Higgs et al. | |
| 2015/0353667 A1* | 12/2015 | Ponrathnam | C08F 228/04 524/547 |

OTHER PUBLICATIONS

National Center for Biotechnology Information. PubChem Compound Database; CID=53401066, https://pubchem.ncbi.nlm.nih.gov/compound/53401066 (accessed Mar. 9, 2016).*
PubChem structure search results, 1 pg, dated Mar. 9, 2016.*
International Search Report and the Written Opinion of the International Searching Authority, PCT/IN2013/000387, Council of Scientific & Industrial Research, Nov. 8, 2013.
International Preliminary Report on Patentability, PCT/IN2013/000387, Council of Scientific & Industrial Research, Oct. 6, 2014.
ISA/EP, International Search Report and Written Opinion prepared for PCT/IN2014/000015 dated Apr. 6, 2014.
International Preliminary Report on Patentability for PCT/IN2014/000015 dated Jan. 30, 2015.

* cited by examiner $^1$H NMR spectra of 2-phenoxy, 2-phenylethyl acrylate, solvent- CDCl$_3$, TMS- standard Figure: 1

Figure: 2

$^{13}$C NMR spectra 2-phenoxy, 2-phenylethyl acrylate, solvent- CDCl$_3$,

IR Spectra of 2-phenoxy, 2-phenylethyl acrylate

Figure: 5

¹H NMR spectra of 2-phenoxy, 2-phenylethyl methacrylate, solvent- CDCl₃, TMS- standard Figure: 6

$^{13}$C NMR spectra 2-phenoxy, 2-phenylethyl methacrylate, solvent- CDCl$_3$,

Figure: 7

$^{13}$C-DEPT NMR spectra 2-phenoxy, 2-phenylethyl methacrylate, solvent- CDCl$_3$,

Figure 8
IR spectra of 2-phenoxy, 2-phenylethyl methacrylate

HIGH REFRACTIVE INDEX (METH) ACRYLATES

FIELD OF THE INVENTION

The present invention relates to high refractive index aromatic hydrophobic monomers of Formula I having a high refractive index. In particular, the present invention relates to an efficient and improved process for the preparation of aromatic hydrophobic monomers of Formula (I), wherein the high refractive index property can be advantageously used to make light weight optical materials with high transparency.

Formula I

BACKGROUND OF THE INVENTION

Amongst several optical properties, refractive index is one of the most important criteria for selection of materials suitable for application in optics. One of the possible candidates for this purpose is plastic materials. Other than the essential properties like light transmission, transparency and refractive index, plastics are also known for their light weight. High refractive index is an important-property required for the manufacture of transparent synthetic resin as optical material. Transparent synthetic resin having high refractive index when used as optical products can be rendered thinner than material having low refractive index to give the same focal distance. The use of thin lenses contributes to reducing the volume of space occupied by lenses in optical assemblies, which can advantageously make an optical apparatus light weight and small sized.

Transparent composite materials are becoming increasingly important in applications ranging from protective coatings to optical communications. Optical materials are useful to control the flow and intensity of light. Examples of useful optical products include optical light fibers, light tubes, optical films including totally internal reflecting films, retroreflective sheeting, ophthalmic lenses. These monomers can be used in compositions to make light management films advantageously provide a cured composition having high refractive index. Even for applications such as liquid crystal displays, adhesives, magnifying lenses, binoculars, and telescopes requires monomers having high refractive index. High refractive index polymers have a wide variety of applications in dentistry, optical eyewear, holography, and microelectronics.

Optical products can be prepared from high index of refraction materials, including monomers such as high index of refraction (meth)acrylate monomers, aromatic based monomers, and other such high index of refraction monomers that are known in the optical product. The monomers can be cured or polymerized to take the form of a product capable of modifying or controlling the flow of light. The preparation of high refractive index monomers and their applications in optical articles are known in the prior arts.

Frunze, T. M et al. in Russian chemical bulletin 19 (1970), S. 183-184 discloses a process for preparation of 2-Allyl-4-phenoxyphenyl methacrylate, by the reacting of 2-allyl-4-phenoxyphenol with methacryloyl chloride, and their properties. Further Michael E. Wright (2010) reported a process for preparation of 3-{(4-phenoxyphenyl)}methyl methacrylate by treating 3-phenoxybenzyl alcohol with methacryloyl chloride.

U.S. Pat. No. 7,714,090 discloses a process for the production of a monoaryl(meth)acrylate compound by reacting the acryloyl compound with the aryloxy alcohol compound in a solvent in the presence of a catalyst. The invention also provides a process for preparation of a soft intraocular lens comprising the (meth)acrylate copolymer having a refractive index of 1.50 to 1.59.

U.S. Pat. No. 5,693,095 discloses an improved soft, foldable acrylic lens materials which are particularly suited for use as intraocular lens (IOLs), but which are also useful as other ophthalmic devices, such as contact lenses, keratoprostheses, and corneal rings or inlays. These materials contain only two principal components: one aryl acrylic hydrophobic monomer which is selected from the group consisting of 2-phenylethyl acrylate and 4-phenylbutyl methacrylate etc. and another hydrophilic monomer which is selected from the group consisting of 2-hydroxyethyl acrylate; 2-hydroxyethyl methacrylate, 2-N-ethylacrylate pyrrolidone, 2-hydroxy-3-phenoxypropyl acrylate etc. Further it comprises additional components, such as cross-linking, UV-light absorbing, and blue-light absorbing components. The copolymer of said patent has a refractive index of at least 1.50.

U.S. Pat. No. 5,290,892 discloses an intraocular lens comprising a copolymer with an elongation of at least 150%, wherein said copolymer is comprised of two monomers, the first of which is 1-phenylethyl acrylate at a concentration about 65 wt. % and the second of which is 2-phenylethyl methacrylate at a concentration of about 30 wt. %., and a copolymerizable cross-linking monomer such as 1,4-butanediol diacrylate having a plurality of polymerizable ethylenically unsaturated groups.

U.S. Pat. No. 5,891,931 relates to methods for preparing foldable acrylic, high refractive index ophthalmic device materials that contain a UV-absorbing chromophore and a benzoyl phosphine oxide photo-initiator which comprises activating the benzoyl phosphine oxide photo-initiator with a blue-light source.

U.S. Pat. No. 7,271,283 discloses a method of making a high refractive index monomer which comprises reacting an aromatic nucleophile with epichlorohydrin to form a disubstituted 2-propanol and reacting the disubstituted 2-propanol with an ethylenically unsaturated reactant to form a high refractive index monomer.

U.S. Pat. No. 8,378,046 provides pressure-sensitive adhesives having a refractive index of at least 1.50, comprising the inter polymerized reaction product of: (a) at least one (meth)acrylic acid ester monomer, (b) at least one monomer containing a substituted or an unsubstituted biphenyl group; and (c) at least one containing an acid functional monomer also provides process for preparation thereof.

WO 2009058513 discloses pressure-sensitive adhesive comprising the inter polymerized reaction product of: (a) at least one (meth)acrylic acid ester monomer, (b) at least one monomer containing a substituted or an unsubstituted carbazole group; and (c) at least one containing an acid functional monomer.

JP 2009280546 provides a new polymerizable di(meth) acrylate compound having a high refractive index and excellent transparency without problems of absorption in the ultraviolet region and fluorescence.

The catalyzed or uncatalyzed reaction of styrene oxide with phenol to form corresponding primary and secondary alcohols is disclosed by Cyrus O. Guss in *J. Am. Chem. Soc.*, 1949, 71 (10), pp 3460-3462. A resin with a high refractive index and a high Abbe number composed of essentially sulfur-containing aromatic methacrylates. An optical material composed of said resin is provided especially for lenses, is reported in *Journal of Applied Polymer Science*, 2000 (76), pp 50-54.

Further, J. McGrath et al. in *Polymer* 2006(47), pp 4042-4057 discloses a novel, high-refractive index homo polymer produced by incorporating carbazole and phenol into the methacrylate monomer structure followed by recrystallization from methanol, produces a good yield of highly pure carbazole phenoxy functionalized methacrylate monomer. Subsequent free radical polymerization or UV photo polymerization of the functionalized methacrylate monomer, in addition to copolymerizations with methyl methacrylate, provided for high-refractive index materials well suited for lightweight optical applications.

Chehade, M. & Helder, M. J., (1997) in A review, ANZ Journal of Opthalmology, 25, 255-263 discloses development of foldable intraocular lens (IDLs) such as hydrogel, soft acrylic, silicon IOL and its clinical perspective.

High refractive index (RI) materials are extremely important in many optical applications. Polymers traditionally have relatively low refractive indices, but they can be raised to technologically useful values. L. Beecroft et al. have prepared RI tunable materials up to 1.68 using brominated and aromatic monomers in a copolymer synthesis method, wherein said copolymers are transparent in the technologically important near-IR, have high glass transition temperatures, and are good film formers which is disclosed in *J. Macromolecular Science A* 1997, 34 (4), pp 573-586.

Current high RI plastics include polyurethanes, polyesters, epoxy and episulfide resins. Most of the high RI plastics use thiourethane and episulfide chemistries with highly polarizable chemical moieties such as aromatics and sulfur. However, optical articles produced from these materials suffer from after-cure yellowing and strong odors released during lens processing. In addition, these monomers have inherently long production cycles due to prolonged curing times needed for maintaining optical homogeneity. Therefore, there is a need for monomers which offer fast cure, high RI, low color, and low odor when cured or upon cutting and grinding, while maintaining optical homogeneity and improved and efficient process for preparation thereof.

It is advantageous that, the novel monomers prepared according to the current process do not need any derivatization or treatment to polymerization to prepare material with high refractive index and excellent transparency property. In particular, the polymeric material prepared from the novel monomer can be used for making thinner optical articles than conventional used ones, with advantages of reduced volume of space and lightweight materials.

Further the aromatic based monomers of the present invention are more hydrophobic as compared to existing hydrophilic intraocular lens (IOLs). It is observed that the hydrophobic lenses which are generally made up of aromatic based materials are better at UV filtration than aliphatic materials based hydrophilic lens. Also surfaces of soft hydrophobic IOLs are smoother than those of soft hydrophilic IOLs and tailorable glass transition temperature is one of the benefits of the present aromatic hydrophobic monomers.

OBJECTS OF THE INVENTION

Main objective of the present invention is to provide high refractive index aromatic hydrophobic monomers of Formula I, which are useful to produce optical materials. Another object of the present invention is to provide an efficient and improved process for the preparation of high refractive index aromatic hydrophobic monomers of Formula I.

Yet another object of the present invention is to provide aromatic hydrophobic monomers of Formula I having high refractive index and transparency, useful for making thinner and light weight optical materials.

SUMMARY OF THE INVENTION

Accordingly, present invention provides a high refractive index, aromatic hydrophobic monomer of Formula (I), Formula I wherein, R is hydrogen or methyl;

R1 is selected from the group consisting of hydrogen, (C1-C6)alkyl, aryl, and trifluromethyl;

R2 is selected from the group consisting of hydrogen, (C1-C6)alkyl, and aryl; and R3 is selected from the group consisting of hydrogen, (C1-C6)alkyl, aryl, and substituted alkyl or aryl group, wherein aryl group is selected from the group consisting of phenyl, benzyl, tolyl, and naphthyl.

In an embodiment of the present invention, there are provided representative compounds of Formula (I) comprising:

i. 2-phenoxy, 2-phenylethyl acrylate (Formula-Ia);

Formula -Ia ii. 2-phenoxy, 2-phenylethyl methacrylate (Formula-Ib).

Formula-Ib

In another embodiment of the present invention, there is provided a monomer having refractive index in the range of 1.55 to 1.57.

In yet another embodiment, present invention provides process for preparation of high refractive index aromatic hydrophobic monomer of Formula (I) comprising: condensing 0.01 to 0.20 moles aromatic alcohol of Formula (III)

Formula III in the presence of 0.05 to 0.25 molar base with 0.05 to 0.30 moles acrylic monomer of Formula (II)

Formula II and optionally in the presence of a solvent, at a temperature ranging between 0° C. to 50° C. to obtain aromatic hydrophobic monomer of Formula (I), wherein, R is hydrogen or methyl; R1 is selected from the group consisting of hydrogen, (C1-C6)alkyl, aryl, and trifluromethyl; R2 is selected from the group consisting of hydrogen, (C1-C6)alkyl, and aryl; R3 is selected from the group consisting of hydrogen, (C1-C6)alkyl, aryl, substituted alkyl, and substituted aryl, wherein aryl is selected from the group consisting of phenyl, benzyl, tolyl, and naphthyl.; and $R_4$ is hydrogen or acetal; $R_5$ is —OH, —OMe, and —Cl.

In yet another embodiment of the present invention, the acrylic monomer of Formula (II) is selected from the group consisting of methacrylic acid, acrylic acid, methyl methacrylate, methyl acrylate, methacryloyl chloride, and acryloyl chloride.

In yet another embodiment of the present invention, the base is an organic base.

In still another embodiment of the present invention, the base is selected from the group consisting of triethylamine, trimethylamine, pyridine, 4-dimethylaminopyridine (DMAP), and aniline.

In another embodiment of the present invention, the base is an inorganic base selected from the group consisting of sodium carbonate, potassium carbonate, sodium hydroxide, potassium hydroxide, sodium hydride, and bicarbonates.

In yet another embodiment of the present invention, the base is an organic amine.

In yet another embodiment of the present invention, the condensation solvent is selected from the group consisting of water, esters, ketones, ethers, alcohols, aromatic hydrocarbons, haloalkanes, and heterocyclic compounds.

In an embodiment of the present invention, the condensation solvent is selected from the group consisting of dichloromethane, tetrahydrofuran, toluene, ethyl methyl ketone, chloroform, ethyl acetate, petroleum ether, and combinations thereof.

In another embodiment of the present invention, the condensation solvent are dry and distilled.

In yet another embodiment of the present invention, the condensation step is performed in the presence of a catalyst.

In yet another embodiment of the present invention, the catalyst is selected from the group consisting of sulphonic acids, sulphuric acid, and polymer supported acid catalyst.

In yet another embodiment of the present invention, the process is maintained at a temperature in the range of 0° C. to 35° C.

In yet another embodiment of the present invention, there is provided use of the high refractive index aromatic hydrophobic monomer for making thinner and light weight optical materials, intraocular lenses with optical diameters up to 6.0 mm.

In yet another embodiment of the present invention, the molar concentration of aromatic alcohol of Formula III is in the range of 0.01 to 0.20 moles.

In still another embodiment of the present invention, the molar concentration of aromatic alcohol of Formula III is in the range of 0.05 to 0.15 moles.

In yet another embodiment of the present invention, the molar concentration of acrylic monomer of Formula II is in the range of 0.05 to 0.30 moles.

In another embodiment of the present invention, the molar concentration of acrylic monomer of Formula II is in the range of 0.07 to 0.23 moles.

In yet another embodiment of the present invention, the molar concentration of base is in the range of 0.05 to 0.25 moles.

In yet another embodiment of the present invention, the aromatic alcohol of Formula (III) is prepared by reacting a nucleophile with an aromatic epoxide in presence of an inorganic base and a solvent.

In yet another embodiment of the present invention, the nucleophile is selected from the group consisting of a phenol, cresol, and trifluromethyl phenol.

In yet another embodiment of the present invention, the aromatic epoxide is selected from the group consisting of styrene oxide, and stilbene oxide.

In yet another embodiment of the present invention, the inorganic base is selected from the group consisting of metal oxides, hydroxides, hydride, and alkoxide.

In still another embodiment of the present invention, the inorganic base is selected from the group consisting of NaOH, KOH, $Na_2CO_3$, $NaHCO_3$, $K_2CO_3$, NaH, and $NaOCH_3$.

In yet another embodiment of the present invention, the molar concentration of the nucleophile is in the range of 0.1 to 0.8 moles.

In yet another embodiment of the present invention, the molar concentration of the epoxide is in the range of 0.01 to 0.5 moles.

In still another embodiment of the present invention, the molar concentration of the inorganic base is in the range of 0.01 to 0.5 moles.

BRIEF DESCRIPTION OF ACCOMPANYING DRAWINGS

FIG. 1 represents ¹H NMR spectra of monomer 2-phenoxy,2-phenylethyl acrylate, solvent-CDCl₃, TMS-standard.

FIG. 2 represents ¹³C NMR spectra of monomer 2-phenoxy,2-phenylethyl acrylate, solvent-CDCl₃.

FIG. 3 represents ¹³C NMR-Distortionless Enhancement by Polarization Transfer (DEPT) spectra of monomer 2-phenoxy,2-phenylethyl acrylate, solvent-CDCl₃.

FIG. 4 represents the spectrogram obtained by Fourier Transform Infra-Red Spectrometry (FTIR) of monomer 2-phenoxy,2-phenylethyl acrylate.

FIG. 5 represents ¹H NMR spectra of monomer 2-phenoxy,2-phenylethyl methacrylate, solvent-CDCl₃,TMS-standard.

FIG. 6 represents ¹³C NMR spectra of monomer 2-phenoxy,2-phenylethyl methacrylate, solvent-CDCl₃.

FIG. 7 represents ¹³C NMR-Distortionless Enhancement by Polarization Transfer (DEPT) spectra of monomer 2-phenoxy,2-phenylethyl methacrylate, solvent-CDCl₃.

DETAILED DESCRIPTION OF INVENTION

Figure 8:
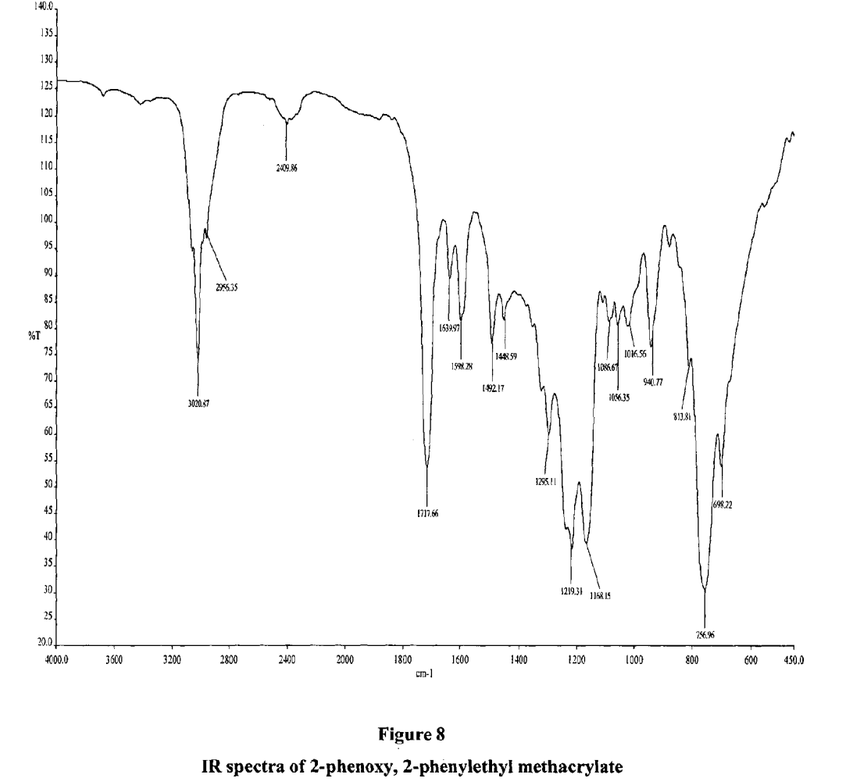
FIG. 8 represents the spectrogram obtained by Fourier Transform Infra-Red Spectrometry (FTIR) of monomer 2-phenoxy,2-phenylethyl methacrylate.

The term "high refractive index" is used to refer to monomers having a refractive index more than 1.55.

Present invention provides high refractive index aromatic hydrophobic monomers of Formula (I):

Formula I wherein, R is hydrogen or methyl; R1 is selected from the group consisting of hydrogen, (C1-C6)alkyl, aryl, triflurom­ethyl; R2 is selected from the group consisting of hydrogen, (C1-C6)alkyl, aryl; and R3 is selected from the group consisting of hydrogen, (C1-C6)alkyl, or aryl or substituted alkyl or aryl group, wherein aryl group is selected from the group consisting of phenyl, benzyl, tolyl, naphthyl.

The invention provides an efficient and improved process for the preparation of aromatic hydrophobic monomers of Formula (I) having high refractive index, comprising condensing aromatic alcohol of Formula (III), in presence of suitable solvent and base;

Formula III wherein, R1, R2 and R3 are defined above and R₄ is hydrogen, acetal;
with acrylic monomer of Formula (II), Formula II wherein, R is defined above and R₅ is —OH, —OMe or —Cl, to obtain high yield of aromatic hydrophobic monomers of (Formula I) with high refractive index and transparency, which is useful for making optical materials like intraocular lenses.

The aromatic alcohol of Formula III, wherein R1 and R2 are identical or independent substituents selected from group consisting of H, (C1-C6)alkyl, halide, hydroxyl, acid, esters, alkoxy, aryl, arylalkyl, substituted alkyl, amines or derivatives thereof, particularly H, (C1-C6)alkyl, hydroxyl, substituted alkyl; whereas R3 substituent selected from group consisting of H, alkyl, aryl, arylalkyl or substituted aryl, aryl group is not restricted to phenyl, benzyl, tolyl, naphthyl etc. and R4 is selected from the group consisting of hydrogen, acetal.

Formula-III

The present invention provides synthesis of aromatic alcohol of Formula (III), comprises reaction of nucleophile with aromatic epoxide in presence of inorganic base and suitable solvent, wherein the nucleophile is selected from group consisting of a phenol, cresol, trifluromethyl phenol, etc. and aromatic epoxide is selected from the group consisting of styrene oxide or stilbene oxide.

The base employed in the nucleophilic reaction is selected from the group consisting of metal oxides, hydroxides, hydride, alkoxide, preferably NaOH, KOH, Na₂CO₃, NaHCO₃, K₂CO₃, NaH or NaOCH₃.

The molar concentration of nucleophile is in the range of 0.1 to 0.8 mol. The inorganic base is used in the molar concentration ranging from 0.01 to 0.5 mol, whereas the molar concentration of epoxide is in the range of 0.01 to 0.5 mol.

The obtained crude product of aromatic alcohol (Formula III) is subsequently purified by recrystallization with organic solvents and used in the preparation of formula I.

Present invention provides the acrylic monomer of Formula II wherein, R substituent is selected from the group consisting of hydrogen, (C1-C6)alkyl, aryl; preferably H or methyl, and R5 substituent is selected from the group consisting of —OH, —OMe, —Cl etc.

Formula II wherein, R is defined above and $R_5$ is —OH, —OMe, —Cl.

Accordingly, the acrylic monomers are selected from methacrylic acid, acrylic acid, methyl methacrylate, methyl acrylate, methacryloyl chloride, acryloyl chloride etc.

The condensation or esterification reaction is optionally performed in presence of catalyst selected from sulphonic acids, sulphuric acid, polymer supported acid catalyst etc.

The aromatic hydrophobic monomers of Formula I are selected from the group consisting of 2-phenoxy,2-phenylethyl acrylate and 2-phenoxy,2-phenylethyl methacrylate and improved process for preparation thereof, Further the obtained monomer having refractive index in the range of 1.48 to 1.58, with enhanced optical properties such as transparency which is useful in optical applications.

The novel high refractive index hydrophobic monomer is 2-phenoxy, 2-phenylethyl acrylate (Formula-Ia), Formula-Ia wherein R is hydrogen, R1, R2 and R3=hydrogen.

Further, the process for the preparation of 2-phenoxy, 2-phenylethyl acrylate of formula Ia comprises condensing 2-phenoxy, 2-phenylethanol with acryloyl chloride in presence of suitable solvent and base. The concentration of 2-phenoxy, 2-phenylethanol and acryloyl chloride used in the reaction is 0.05 to 0.15 and 0.07 to 0.23 respectively. The yield of the final product i.e. 2-phenoxy, 2-phenylethyl acrylate obtained is in the range of 80% to 98%.

The novel high refractive index hydrophobic monomer is 2-phenoxy, 2-phenylethyl methacrylate (Formula-Ib).

Formula-Ib wherein R is methyl, R1, R2 and R3=hydrogen.

Accordingly, the process for the preparation of 2-phenoxy, 2-phenylethyl methacrylate comprises condensing 2-phenoxy, 2-phenylethanol with methacryloyl chloride in presence of suitable solvent and base. The concentration of 2-phenoxy, 2-phenylethanol and methacryloyl chloride used in the condensation/esterification reaction is 0.05 to 0.15 mol and 0.07 to 0.23 mol respectively. Further the yield of 2-phenoxy, 2-phenylethyl methacrylate obtained is in more than 65%. The higher refractive index of present aromatic based hydrophobic monomer of Formula I is in the range of 1.48 to 1.58, particularly 1.48 to 1.55, and hence provides thinner and lighter optical articles like intraocular lenses with excellent transparency.

Subsequently, the completion of the condensation or esterification reaction is monitored by known chromatographic techniques, such as Thin Layer Chromatography, High performance liquid chromatography.

The lower alcohols are employed to deactivate the unreacted acrylic monomer of Formula II, while keeping the temperature below room temperature, particularly below 20° C., wherein the lower alcohol is selected from methanol, ethanol, propanol, butanol or isopropanol. The concentration of alcohol used in the reaction is in the range of 0.01 to 0.2 mol.

Typically in the reaction to prepare high refractive index monomers, the product contains impurities. The removal of color from the prepared monomers may be carried out by column chromatography using silica gel as absorbent and petroleum ether:ethyl acetate mixture as a solvent.

The aromatic based hydrophobic monomers with high refractive index of present invention will be used as co-monomer for making copolymers that have higher refractive index. These co-polymers are currently used for making optical materials like intraocular lenses (IOLs). Such IOLs are flexible enough to be folded and placed through a small incision. In the eye the lens will slowly unfold to be its original shape and prescribed optical quality within 24 hrs. The higher refractive index (1.48 to 1.58) allows these lenses to have optical diameters up to 6.0 mm and yet still be thin enough to fold tightly and pass through a small incision.

EXAMPLES

Following examples are given by way of illustration therefore should not be construed to limit the scope of the invention.

Example-1

Synthesis of 2-phenoxy, 2-phenylethyl alcohol

In a three necked round bottom flask equipped with stirrer, condenser and a dropping funnel was charged 28.2 g (0.3 mol) of phenol, 4 g (0.1 mol) of NaOH and 15 mL of water. Mixture was kept stirring at 80° C. for 10 min. As soon as mixture becomes homogeneous 12.01 g (0.1 mol) of styrene oxide was added drop wise. Reaction mixture was refluxed with stirring at 100° C. for three hours. After completion of reaction amber colored reaction mixture was cooled to 20° C. and added drop wise to cold 5% NaOH (150 mL) solution to remove excess of free phenol. The insoluble material then taken up in to 100 mL of dichloromethane. Organic layer was washed with 5% NaOH (100 mL) solution followed by brine and water. Further organic layer dried over anhydrous sodium sulphate and dichloromethane was removed under reduced pressure. Viscous amber colored liquid turns light brown solid on cooling. The crude product was purified by recrystallization with petroleum ether:dichloromethane (90:10) mixture to obtain 15.0 g of pure 2-phenoxy, 2-phenylethyl alcohol as white solid.

Example-2

Synthesis of 2-phenoxy, 2-phenylethyl alcohol

In a three necked round bottom flask equipped with stirrer, condenser and a dropping funnel was charged 14.1 g (0.15 mol) of phenol, 2 g (0.05 mol) of KOH and 7 mL of water. Mixture was kept stirring at 80° C. for 10 min. As soon as mixture becomes homogeneous 6.0 g (0.05 mol) of styrene oxide was added drop wise. Reaction mixture was refluxed with stirring at 100° C. for three hours. After completion of reaction amber colored reaction mixture was cooled to 20° C. and added drop wise to cold 5% NaOH (70 mL) solution to remove excess of free phenol. The insoluble material then taken up in to 50 mL of dichloromethane. Organic layer was washed with 5% NaOH (50 mL) solution followed by brine and water. Further organic layer dried over anhydrous sodium sulphate and dichloromethane was removed under reduced pressure. Viscous amber colored liquid turns light brown solid on cooling. The crude product was purified by recrystallization with petroleum ether:dichloromethane (90:10) mixture to obtain 7.40 g of pure 2-phenoxy, 2-phenylethyl alcohol as white solid.

Example-3

Synthesis of 2-phenoxy, 2-phenylethyl acrylate

In a three necked flask equipped with a mechanical stirrer, nitrogen inlet, and guard tube was charged 32.8 g (0.15 mol) of 2-phenoxy, 2-phenylethanol, 100 ml of dry distilled dichloromethane. The reaction flask was cooled in an ice bath under nitrogen. 23.7 g (0.23 mol) triethylamine was added by dropping funnel under stirring. Acryloyl chloride 21.04 g (0.23 mol) in 100 ml dry dichloromethane was taken in dropping funnel, added slowly, drop wise with stirring maintaining temperature 0-5° C. throughout the addition. After the addition reaction mixture was kept stirring at same temperature for 2 hours. Reaction further proceeds at room temperature for 24 hours. Reaction was monitored by TLC (30% DCM in hexane). After completion of reaction 3.20 g (0.1 mol) of methanol was added dropwise to deactivate the unreacted acryloyl chloride while keeping the temperature below 20° C. Then, 200 mL of water was added thereto to wash the mixture, followed by separation of the mixture into layers. Thereafter organic layer was washed with 4% NaOH solution, brine solution and distilled water. Organic layer was dried over sodium sulphate and dichloromethane was removed under reduced pressure to obtain liquid 2-phenoxy, 2-phenylethyl acrylate. Crude product was purified by column chromatography (silica gel) using petroleum ether:ethyl acetate (90:10) mixture to yield 39.0 g of colorless transparent liquid. The yield was 95% based on the charged 2-phenoxy, 2-phenylethanol. Monomer is having refractive index 1.565.

Example-4

Synthesis of 2-phenoxy, 2-phenylethyl acrylate

In a three necked flask equipped with a mechanical stirrer, nitrogen inlet, and guard tube was charged 32.8 g (0.15 mol) of 2-phenoxy, 2-phenylethanol, 100 ml of dry distilled dichloromethane. The reaction flask was cooled in an ice bath under nitrogen. 16.19 g (0.16 mol) triethylamine was added by dropping funnel under stirring. Acryloyl chloride 14.64 g (0.16 mol) in 70 ml dry dichloromethane was taken in dropping funnel, added slowly, drop wise with stirring maintaining temperature 30° C. throughout the addition. After the addition reaction mixture was kept stirring at same temperature for 2 hours. Reaction further proceeds at room temperature for 24 hours. Reaction was monitored by TLC (30% DCM in hexane). After completion of reaction 3.20 g (0.1 mol) of methanol was added dropwise to deactivate the unreacted acryloyl chloride while keeping the temperature below 20° C. Then, 200 mL of water was added thereto to wash the mixture, followed by separation of the mixture into layers. Thereafter organic layer was washed with 4% NaOH solution, brine solution and distilled water. Organic layer was dried over sodium sulphate and dichloromethane was removed under reduced pressure to obtain liquid 2-phenoxy, 2-phenylethyl acrylate. Crude product was purified by column chromatography (silica gel) using petroleum ether:ethyl acetate (90:10) mixture to yield 36.90 g of colorless transparent liquid. The yield was 90% based on the charged 2-phenoxy, 2-phenylethanol. Monomer is having refractive index 1.565.

Example-5

Synthesis of 2-phenoxy, 2-phenylethyl acrylate

In a three necked flask equipped with a mechanical stirrer, nitrogen inlet, and guard tube was charged 32.8 g (0.15 mol) of 2-phenoxy, 2-phenylethanol, 100 ml of dry distilled ethyl methyl ketone. The reaction flask was cooled in an ice bath under nitrogen. 16.19 g (0.16 mol) triethylamine was added by dropping funnel under stirring. Acryloyl chloride 14.64 g (0.16 mol) in 70 ml dry ethyl methyl ketone was taken in dropping funnel, added slowly, drop wise with stirring maintaining temperature 0-5° C. throughout the addition. After the addition reaction mixture was kept stirring at same temperature for 2 hours. Reaction further proceeds at room temperature for 24 hours. Reaction was monitored by TLC (30% DCM in hexane). After completion of reaction 3.20 g (0.1 mol) of methanol was added dropwise to deactivate the unreacted acryloyl chloride while keeping the temperature below 20° C. Then, 200 mL of water was added thereto to wash the mixture, followed by separation of the mixture into layers. Thereafter organic layer washed was with 4% NaOH solution, brine solution and distilled water. Organic layer was dried over sodium sulphate and solvent was removed under reduced pressure to obtain liquid 2-phenoxy, 2-phenylethyl acrylate. Crude product was purified by column chromatography (silica gel) using petroleum ether:ethyl acetate (90:10) mixture to yield 30.50 g of colorless transparent liquid. The yield was 82.65% based on the charged 2-phenoxy, 2-phenylethanol. Monomer is having refractive index 1.565.

Example-6

Synthesis of 2-phenoxy, 2-phenylethyl acrylate

In a three necked flask equipped with a mechanical stirrer, nitrogen inlet, and guard tube was charged 16.4 g (0.075 mol) of 2-phenoxy, 2-phenylethanol, 60 ml of dry distilled tetrahydrofuran. The reaction flask was cooled in an ice bath under nitrogen. 15.5 g (0.15 mol) triethylamine was added by dropping funnel under stirring. Acryloyl chloride 10.52 g (0.12 mol) in 50 ml dry tetrahydrofuran was taken in dropping funnel, added slowly, drop wise with stirring maintaining temperature 0-5° C. throughout the addition. After the addition reaction mixture was kept stirring at same temperature for 2 hours. Reaction further proceeds at room temperature for 24 hours. Reaction was monitored by TLC (30% DCM in hexane). After completion of reaction 1.60 g (0.05 mol) of methanol was added dropwise to deactivate the unreacted acryloyl chloride while keeping the temperature below 20° C. Then, 100 mL of water was added thereto to wash the mixture, followed by separation of the mixture into layers. Thereafter organic layer was washed with 4% NaOH solution, brine solution and distilled water. Organic layer was dried over sodium sulphate and tetrahydrofuran was removed under reduced pressure to obtain liquid 2-phenoxy, 2-phenylethyl acrylate. Crude product was purified by column chromatography (silica gel) using petroleum ether:ethyl acetate (90:10) mixture to yield 19.05 g of colorless transparent liquid. The yield was 93% based on the charged 2-phenoxy, 2-phenylethanol. Monomer is having refractive index 1.565.

Example-7

Synthesis of 2-phenoxy, 2-phenylethyl acrylate

In a three necked flask equipped with a mechanical stirrer, nitrogen inlet, and guard tube was charged 32.8 g (0.15 mol) of 2-phenoxy, 2-phenylethanol, 100 ml of dry distilled dichloromethane. The reaction flask was cooled in an ice bath under nitrogen. 23.7 g (0.23 mol) triethylamine was added by dropping funnel under stirring. Acryloyl chloride 21.04 g (0.23 mol) in 100 ml dry dichloromethane was taken in dropping funnel, added slowly, drop wise with stirring maintaining temperature 0-5° C. throughout the addition. After the addition reaction mixture was kept stirring at same temperature for 2 hours. Reaction further proceeds at room temperature for 10 hours. Reaction was monitored by TLC (30% DCM in hexane). After completion of reaction 3.20 g (0.1 mol) of methanol was added dropwise to deactivate the unreacted acryloyl chloride while keeping the temperature below 20° C. Then, 200 mL of water was added thereto to wash the mixture, followed by separation of the mixture into layers. Thereafter organic layer was washed with 4% NaOH solution, brine solution and distilled water. Organic layer was dried over sodium sulphate and dichloromethane was removed under reduced pressure to obtain liquid 2-phenoxy, 2-phenylethyl acrylate. Crude product was purified by column chromatography (silica gel) using petroleum ether: ethyl acetate (90:10) mixture to yield 36.90 g of colorless transparent liquid. The yield was 90% based on the charged 2-phenoxy, 2-phenylethanol. Monomer is having refractive index 1.565.

Example-8

Synthesis of 2-phenoxy, 2-phenylethyl acrylate

In a three necked flask equipped with a mechanical stirrer, nitrogen inlet, and guard tube was charged 10.93 g (0.05 mol) of 2-phenoxy, 2-phenylethanol, 20 ml of dry distilled dichloromethane. The reaction flask was cooled in an ice bath under nitrogen. 5.55 g (0.07 mol) pyridine was added by dropping funnel under stirring. Acryloyl chloride 7.13 g (0.07 mol) in 20 ml dry dichloromethane was taken in dropping funnel, added slowly, drop wise with stirring maintaining temperature 0-5° C. throughout the addition. After the addition reaction mixture was kept stirring at same temperature for 2 hours. Reaction further proceeds at room temperature for 8 hours. Reaction was monitored by TLC (30% DCM in hexane). After completion of reaction 1.50 g of methanol was added dropwise to deactivate the unreacted acryloyl chloride while keeping the temperature below 20° C. Then, 50 mL of water was added thereto to wash the mixture, followed by separation of the mixture into layers. Thereafter organic layer was washed with 4% NaOH solution, brine solution and distilled water. Organic layer was dried over sodium sulphate and dichloromethane was removed under reduced pressure to obtain liquid 2-phenoxy, 2-phenylethyl acrylate. Crude product was purified by column chromatography (silica gel) using petroleum ether:ethyl acetate (90:10) mixture to yield 13.0 g of colorless transparent liquid. The yield was 95% based on the charged 2-phenoxy, 2-phenylethanol. Monomer is having refractive index 1.565.

Example-9

Synthesis of 2-phenoxy, 2-phenylethyl methacrylate

In a three necked flask equipped with a mechanical stirrer, nitrogen inlet, and guard tube was charged 32.8 g (0.15 mol) of 2-phenoxy, 2-phenylethanol, 100 ml of dry distilled dichloromethane. The reaction flask was cooled in an ice bath under nitrogen. 24.28 g (0.24 mol) triethylamine was added by dropping funnel under stirring. Methacryloyl chloride 24.04 g (0.23 mol) in 100 ml dry dichloromethane was taken in dropping funnel, added slowly, drop wise with stirring maintaining temperature 0-5° C. throughout the addition. After the addition reaction mixture was kept stirring at same temperature for 2 hours. Reaction further proceeds at room temperature for 24 hours. Reaction was monitored by TLC (30% DCM in hexane). After completion of reaction 3.20 g (0.1 mol) of methanol was added dropwise to deactivate the unreacted methacryloyl chloride while keeping the temperature below 20° C. Then, 200 mL of water was added thereto to wash the mixture, followed by separation of the mixture into layers. Thereafter organic layer was washed with 4% NaOH solution, brine solution and distilled water. Organic layer was dried over sodium sulphate and dichloromethane was removed under reduced pressure to obtain liquid 2-phenoxy, 2-phenylethyl acrylate. Crude product was purified by column chromatography (silica gel) using petroleum ether:ethyl acetate (90:10) mixture to yield 39.7 g of colorless transparent liquid. The yield was 92% based on the charged 2-phenoxy, 2-phenylethanol. Monomer is having refractive index 1.568.

Example-10

Synthesis of 2-phenoxy, 2-phenylethyl methacrylate

In a three necked flask equipped with a mechanical stirrer, nitrogen inlet, and guard tube was charged 21.42 g (0.10 mol) of 2-phenoxy, 2-phenylethanol, 50 ml of dry distilled dichloromethane. The reaction flask was cooled in an ice bath under nitrogen. 11.13 g (0.11 mol) triethylamine was added by dropping funnel under stirring. Methacryloyl chloride 11.50 g (0.11 mol) in 50 ml dry dichloromethane was taken in dropping funnel, added slowly, drop wise with stirring maintaining temperature 28° C. throughout the addition. After the addition reaction mixture was kept stirring at same temperature for 2 hours. Reaction further proceeds at room temperature for 24 hours. Reaction was monitored by TLC (30% DCM in hexane). After completion of reaction 1.60 g (0.05 mol) of methanol was added dropwise to deactivate the unreacted methacryloyl chloride while keeping the temperature below 20° C. Then, 100 mL of water was added thereto to wash the mixture, followed by separation of the mixture into layers. Thereafter organic layer was washed with 4% NaOH solution, brine solution and distilled water. Organic layer was dried over sodium sulphate and dichloromethane was removed under reduced pressure to obtain liquid 2-phenoxy, 2-phenylethyl acrylate. Crude product was purified by column chromatography (silica gel) using petroleum ether:ethyl acetate (90:10) mixture to yield 25.9 g of colorless transparent liquid. The yield was 92% based on the charged 2-phenoxy, 2-phenylethanol. Monomer is having refractive index 1.568.

Example-11

Synthesis of 2-phenoxy, 2-phenylethyl methacrylate

In a three necked flask equipped with a mechanical stirrer, nitrogen inlet, and guard tube was charged 32.8 g (0.15 mol) of 2-phenoxy, 2-phenylethanol, 100 ml of dry distilled tetrahydrofuran. The reaction flask was cooled in an ice bath under nitrogen. 24.28 g (0.24 mol) triethylamine was added by dropping funnel under stirring. Methacryloyl chloride 24.04 g (0.23 mol) in 100 ml dry tetrahydrofuran was taken in dropping funnel, added slowly, drop wise with stirring maintaining temperature 0-5° C. throughout the addition. After the addition reaction mixture was kept stirring at same temperature for 2 hours. Reaction further proceeds at room temperature for 24 hours. Reaction was monitored by TLC (30% DCM in hexane). After completion of reaction 3.20 g (0.1 mol) of methanol was added dropwise to deactivate the unreacted methacryloyl chloride while keeping the temperature below 20° C. Then, 200 mL of water was added thereto to wash the mixture, followed by separation of the mixture into layers. Thereafter organic layer was washed with 4% NaOH solution, brine solution and distilled water. Organic layer was dried over sodium sulphate and tetrahydrofuran was removed under reduced pressure to obtain liquid 2-phenoxy, 2-phenylethyl acrylate. Crude product was purified by column chromatography (silica gel) using petroleum ether:ethyl acetate (90:10) mixture to yield 39.7 g of colorless transparent liquid. The yield was 92% based on the charged 2-phenoxy, 2-phenylethanol. Monomer is having refractive index 1.568.

Example-12

Synthesis of 2-phenoxy, 2-phenylethyl methacrylate

In a three necked flask equipped with a mechanical stirrer, nitrogen inlet, and guard tube was charged 10.82 g (0.05 mol) of 2-phenoxy, 2-phenylethanol, 25 ml of dry distilled chloroform. The reaction flask was cooled in an ice bath under nitrogen. 8.01 g (0.08 mol) triethylamine was added by dropping funnel under stirring. Methacryloyl chloride 8.0 g (0.076 mol) in 25 ml dry chloroform was taken in dropping funnel, added slowly, drop wise with stirring maintaining temperature 0-5° C. throughout the addition. After the addition reaction mixture was kept stirring at same temperature for 2 hours. Reaction further proceeds at room temperature for 24 hours. Reaction was monitored by TLC (30% DCM in hexane). After completion of reaction 1.05 g (0.03 mol) of methanol was added dropwise to deactivate the unreacted methacryloyl chloride while keeping the temperature below 20° C. Then, 50 mL of water was added thereto to wash the mixture, followed by separation of the mixture into layers. Thereafter organic layer was washed with 4% NaOH solution, brine solution and distilled water. Organic layer was dried over sodium sulphate and chloroform was removed under reduced pressure to obtain liquid 2-phenoxy, 2-phenylethyl acrylate. Crude product was purified by column chromatography (silica gel) using petroleum ether:ethyl acetate (90:10) mixture to yield 13.10 g of colorless transparent liquid. The yield was 92% based on the charged 2-phenoxy, 2-phenylethanol. Monomer is having refractive index 1.568.

Example-13

Synthesis of 2-phenoxy, 2-phenylethyl methacrylate

In a three necked flask equipped with a mechanical stirrer, nitrogen inlet, and guard tube was charged 32.8 g (0.15 mol) of 2-phenoxy, 2-phenylethanol, 100 ml of dry distilled dichloromethane. The reaction flask was cooled in an ice bath under nitrogen. 33.17 g (0.24 mol) potassium carbonate was added gradually under stirring. Methacryloyl chloride 24.04 g (0.23 mol) in 100 ml dry dichloromethane was taken in dropping funnel, added slowly, drop wise with stirring maintaining temperature 0-5° C. throughout the addition. After the addition reaction mixture was kept stirring at same temperature for 2 hours. Reaction further proceeds at room temperature for 24 hours. Reaction was monitored by TLC (30% DCM in hexane). After completion of reaction 3.20 g (0.1 mol) of methanol was added dropwise to deactivate the unreacted methacryloyl chloride while keeping the temperature below 20° C. Then, 200 mL of water was added thereto to wash the mixture, followed by separation of the mixture into layers. Thereafter organic layer was washed with 4% NaOH solution, brine solution and distilled water. Organic layer was dried over sodium sulphate and dichloromethane was removed under reduced pressure to obtain liquid 2-phenoxy, 2-phenylethyl acrylate. Crude product was purified by column chromatography (silica gel) using petroleum ether:ethyl acetate (90:10) mixture to yield 28.08 g of colorless transparent liquid. The yield was 65% based on the charged 2-phenoxy, 2-phenylethanol. Monomer is having refractive index 1.568.

Comparative Example

| COMPOUNDS | REFRACTIVE INDEX |
| --- | --- |
| 2-PHENOXY, 2-PHENYLETHYL ACRYLATE (Novel Compound) | 1.565 |
| 2-PHENOXY, 2-PHENYLETHYL METHACRYLATE (Novel Compound) | 1.568 |

-continued

| COMPOUNDS | REFRACTIVE INDEX |
|---|---|
| 2-PHENYLETHYL ACRYLATE (Known Compound) | 1.509 |
| 2-PHENYLETHYL METHACRYLATE (Known Compound) | 1.508 |
| 2-PHENOXYETHYL METHACRYLATE (Known Compound) | 1.513 |

A higher refractive index was achieved for new (meth) acrylate monomers by incorporation of polarisable and aromatic ring in their structures. Refractive index of new monomers is significantly improved in comparison to known monomers listed in Table.

ADVANTAGES OF THE INVENTION

The novel monomers prepared according to the process of the invention lead to aromatic based hydrophobic monomers with high refractive index.

The monomers prepared as per the process of invention obviate any derivatization or treatment to polymerization to prepare materials with high refractive index and excellent transparency properties.

The polymers prepared from monomers as per the process of invention can be used for making optical articles such as intraocular lenses.

We claim:

1. An aromatic hydrophobic monomer of Formula (I) having a refractive index≥1.55,

Formula (I)

wherein, R is hydrogen or methyl;
$R^1$ is hydrogen;
$R^2$ is hydrogen; and
$R^3$ is hydrogen.

2. The aromatic hydrophobic monomer as claimed in claim 1, wherein the refractive index of said monomer is in the range of 1.55 to 1.58.

3. The aromatic hydrophobic monomer as claimed in claim 1 for use in making thinner and light weight optical materials, wherein the optical materials are intraocular lenses with optical diameters up to 6.0 mm.

4. A process for the preparation of an aromatic hydrophobic monomer of Formula (I) having a refractive index≥1.55 as claimed in claim 1, said process comprising: condensing 0.01 to 0.20 moles of an aromatic alcohol of Formula (III)

Formula (III)

in the presence of 0.05 to 0.25 molar moles of a base with 0.05 to 0.30 moles of an acrylic monomer of Formula (II)

Formula (II)

and optionally in the presence of a solvent, at a temperature ranging between 0° C. to 50° C. to obtain the aromatic hydrophobic monomer of Formula (I) having a refractive index≥1.55, Formula (I)

wherein, R is hydrogen or methyl;
$R_1$ is hydrogen;
$R_2$ is hydrogen;
$R_3$ is hydrogen;
$R_4$ is hydrogen or acetyl; and
$R_5$ is selected from the group consisting of —OH, —OMe, and —Cl.

5. The process as claimed in claim 4, wherein said condensation step is performed in the presence of a catalyst.

6. The process as claimed in claim 5, wherein said catalyst is selected from the group consisting of sulphonic acids, sulphuric acid, and a polymer supported acid catalyst.

7. The process as claimed in claim 4, wherein said base is selected from the group consisting of an organic base and an inorganic base.

8. The process as claimed in claim 7, wherein said organic base is an organic amine.

9. The process as claimed in claim 8, wherein said organic amine is selected from the group consisting of triethylamine, trimethylamine, pyridine, 4-dimethylaminopyridine (DMAP), and aniline.

10. The process as claimed in claim 7, wherein said inorganic base is selected from the group consisting of sodium carbonate, potassium carbonate, sodium hydroxide, potassium hydroxide, sodium hydride, and bicarbonates.

11. The process as claimed in claim 4, wherein said solvent is selected from the group consisting of water, esters, ketones, ethers, alcohols, aromatic hydrocarbons, haloalkanes, and heterocyclic compounds.

12. The process as claimed in claim 4, wherein said solvent is dry and distilled and said solvent is selected from the group consisting of dichloromethane, tetrahydrofuran, toluene, ethyl methyl ketone, chloroform, ethyl acetate, petroleum ether, and combinations thereof.

13. The process as claimed in claim 4, wherein said process is maintained at a temperature in the range of 0° C. to 35° C.

* * * * *